(12) United States Patent
Golini

(10) Patent No.: US 9,216,160 B2
(45) Date of Patent: Dec. 22, 2015

(54) CHOLINE COMPOSITION

(71) Applicant: Jeffrey M. Golini, Billings, MT (US)

(72) Inventor: Jeffrey M. Golini, Billings, MT (US)

( * ) Notice: Subject to any disclaimer, the term of this patent is extended or adjusted under 35 U.S.C. 154(b) by 0 days.

(21) Appl. No.: 13/261,836

(22) PCT Filed: Oct. 4, 2012

(86) PCT No.: PCT/US2012/000481
§ 371 (c)(1),
(2) Date: Mar. 26, 2014

(87) PCT Pub. No.: WO2013/052117
PCT Pub. Date: Apr. 11, 2013

(65) Prior Publication Data
US 2015/0164828 A1    Jun. 18, 2015

Related U.S. Application Data

(60) Provisional application No. 61/626,928, filed on Oct. 5, 2011.

(51) Int. Cl.
| *A61K 31/14* | (2006.01) |
|---|---|
| *A61K 31/198* | (2006.01) |
| *A61K 31/455* | (2006.01) |
| *A61K 31/519* | (2006.01) |

(52) U.S. Cl.
CPC .............. *A61K 31/14* (2013.01); *A61K 31/198* (2013.01); *A61K 31/455* (2013.01); *A61K 31/519* (2013.01)

(58) Field of Classification Search
CPC .................................................... A61K 31/14
USPC ....................................................... 514/249
See application file for complete search history.

(56) References Cited

U.S. PATENT DOCUMENTS

| 4,237,118 | A | 12/1980 | Howard |
|---|---|---|---|
| 4,911,917 | A | 3/1990 | Kuhrts |
| 5,084,482 | A | 1/1992 | Hirsch et al. |
| 5,215,750 | A | 6/1993 | Keane, II |
| 5,597,585 | A | 1/1997 | Williams et al. |
| 6,080,428 | A | 6/2000 | Bova |
| 6,090,839 | A | 7/2000 | Adams et al. |
| 7,304,044 | B2 | 12/2007 | Jarowski |
| 7,875,291 | B1 | 1/2011 | Habib et al. |
| 2006/0009486 | A1 | 1/2006 | Mitchell |
| 2007/0037818 | A1 | 2/2007 | Livingston |
| 2007/0065456 | A1 | 3/2007 | Woods |
| 2007/0160590 | A1 | 7/2007 | McCleary |
| 2007/0178216 | A1 | 8/2007 | Kandaswami et al. |
| 2007/0196496 | A1 | 8/2007 | Farber et al. |
| 2010/0009006 | A1 | 1/2010 | Hill et al. |
| 2010/0021573 | A1 | 1/2010 | Gonzalez et al. |
| 2010/0055182 | A1 | 3/2010 | Gastner et al. |
| 2010/0080856 | A1 | 4/2010 | Constantino |

FOREIGN PATENT DOCUMENTS

| CA | 2057463 | A1 | 6/1993 |
|---|---|---|---|
| CA | 1333997 | | 1/1995 |
| CN | 101721421 | A | 6/2010 |
| CZ | 294623 | B6 | 2/2005 |
| EP | 1310253 | | 5/2003 |
| EP | 1859690 | A1 | 11/2007 |
| FR | 2851425 | | 8/2004 |
| GB | 1159615 | | 7/1969 |
| JP | 6024977 | | 2/1994 |
| WO | WO 99/65337 | | 12/1999 |
| WO | WO 2007/053773 | | 5/2007 |
| WO | WO 2007/069827 | | 6/2007 |
| WO | WO 2008/134645 | | 11/2008 |

OTHER PUBLICATIONS

Kamanna et al., "Mechanism of Action of Niacin," *Am. J. Cardiol.* 101(Suppl.):20B-26B, 2008.

Pieper, "Overview of niacin formulations: Differences in pharmacokinetics, efficacy, and safety," *Am. J. Health-Syst-Pharm* 60(Suppl 2):S9-S14, 2003.

*Primary Examiner* — Taofiq A Solola
(74) *Attorney, Agent, or Firm* — Seed IP Law Group PLLC

(57) ABSTRACT

Compositions and methods for treating hyperlipidemia and elevated LDL cholesterol and for weight reduction are disclosed. The compositions comprise
(a) choline, or a salt or hydroxide thereof;
(b) niacin, or a salt, amide or ester thereof;
(c) folic acid, or a salt thereof;
(d) methionine or a salt or ester thereof; and
(e) glycine or a salt, ester or methylated form thereof.

21 Claims, No Drawings

CHOLINE COMPOSITION

This application claims the benefit of provisional application Ser. No. 61/626,928 filed Oct. 5. 2011.

TECHNICAL FIELD

The invention relates to a composition for treating hyperlipidemia, reducing LDL cholesterol and/or reducing body fat in humans.

BACKGROUND OF THE INVENTION

A 'Fat' Conundrum

The human body is made from the simplest of starting materials—carbon, water, oxygen and nitrogen—assembled and organized into nearly infinite structural complexities. Of all our body's complexities, the seemingly simple fat is indispensible to life itself. It alone is responsible for compartmentalizing cells and organs, as well as insulating our neural network and preventing a biological 'short circuit'. In other words, we are essentially kept alive by fats.

Lipid (fats) are essential for life support. Lipids provide biological energy to burn, protect internal organs, aid in nutrient absorption, and are the starting material for hormones and some vitamins. Lipids can be simple or complex. They come in a variety of forms, and are generally categorized into several families as fats, oils, phospholipids, sterols, triglycerides or waxes. No matter the family, all lipids share the same trait of insolubility in water and soluble in numerous organic solvents.

Several members of two very important lipid families—the simple lipid cholesterol (high density lipoproteins [HDL], low density lipoproteins [LDL], and related fatty acids), and triglycerides—a complex lipid, have been linked to an ever increasing list of health concerns.

Good Lipids Gone 'Bad'

While the liver is capable of synthesizing all needed lipid complexes from plant matter, humans usually assist this natural process by indulging in gross excesses of commercially available fats.

There are predominantly four types of fats in the foods we eat. Saturated and trans fats (both of which are considered undesirable because of the way they are treated during assimilation) have been shown to raise low density lipoprotein (LDL) cholesterol ('bad cholesterol') levels in the blood; monounsaturated and polyunsaturated fats are not identified by our metabolic processes in the same manner, and do not appear to negatively impact LDL when consumed in moderation.

Excess calories (from fats, carbohydrates, and protein [to a lesser degree]) are all eventually stored as fat (adipose tissue). The cycle of hyperlipidemia (elevated serum cholesterol) begins with the synthesis of bile acid in the liver, from existing cholesterol, in response to caloric intake. As intake increases, more bile acid is produced. This material functions like an organic 'soap', forming a protective envelope around otherwise insoluble food fats (saturated and excess unsaturated fats), permitting digestion and assimilation. At the end of the cycle (in the ileum) they are 'uncoupled' (deconjugated) reabsorbed and recycled. This action increases the total amount of cholesterol in the blood plasma.

Storing of energy reserve is one of the body's 'survival mechanisms'. Excess carbohydrates (simple/complex sugars) and protein not burned are all primarily converted to triglycerides and stored in fats cells. Excess of triglycerides in the plasma is called hypertriglyceridemia and is also linked to the occurrence of coronary artery disease.

Hyperlipidemia and Heart Disease

Elevated blood cholesterol (LDL and triglycerides) levels initiate arteriosclerosis and (potentially) hypertension. While it is not a universal association, hyperlipidemia is most often observed in conjunction with being overweight.

Data from the National Health and Nutrition Examination Survey (NHANES) completed in 2001-2004 showed that about two thirds of all adults in the United States were overweight and almost one-third was obese. According to a most recent cumulative study conducted by the CDC and NHANES, it was discovered that the number of cases of adult obesity has reach 68% (Ogden C L, Carroll M D, McDowell M A, Flegal K M; Obesity among adults in the United States—no change since 2003-2004. NCHS data brief no 1. Hyattsville, Md.: National Center for Health Statistics; 2007). The CDC has estimated that obesity is fast approaching tobacco as the top underlying preventable cause of death in the USA.

In 2000, poor diet including obesity and physical inactivity caused around 400,000 U.S. deaths, which is more than 16% of all deaths and the number two killer. That compares with 435,000 for tobacco or 18%, which is the top (self inflicted) underlying preventable killer.

In 2004, obesity mixed with inactivity increases the risks for the top two killers: all forms of cardiovascular disease (heart/disease and/or attack, cerebrovascular events—including stroke), and all forms of malignancies (National Vital Statistics Report, Volume 53, Number 5; October 2004.). As of 2004, the Journal of the American Medical Association listed '*mistakes caused by the actions of health professionals*' the third leading cause of (preventable) death in the USA, beating out tobacco (Journal Of The American Medical Association; Starfield, B; 284(4):483-485; 2000).

In addition, hyperlipidemia and obesity are strong risk factors for hypertension (today more than 50 million Americans have hypertension), diabetes, kidney disease, gastric related disease, gallbladder disease, osteoarthritis, sexual dysfunction (ED), sleep apnea and other breathing problems.

The Statins Paradox

Presently, the number one drug in the pharmaceutical industry for antilipidemic action is the statin drug. This drug, created approximately 20 years ago, acts by inhibiting 3-hydroxy-3-methylglutaryl-Co enzyme (HMG-CoA reductase), the enzyme that leads to production of cholesterol. As production declines, a deficit in the total cholesterol pool forms causing the body to draw on its lipid reserves. The statin drug also has a second effect, it acts as an anti-inflammatory. Despite manufactures claims that HMG-CoA reductase inhibition is the primary reason for the cardiovascular benefit, there is now a growing body of evidence to suggest that it is not the case (Shovman. Immunol Res, 25(3); 2002).

Unfortunately this type of drug has a very negative downside. By blocking cholesterol synthesis, it directly causes the depletion of other key biological components downstream such as, ubiquinol (coenzyme Q10), creation and phosphorylation of various lipids, and muscle enzymes. Persistent muscle pain and weakness are the signs and symptoms of statin actions on these pathways. A review of the packing inserts for the most common statin cholesterol drugs available gives a list of the most common side effects that have been seen: unexplained muscle pain and weakness, headache, muscle aches, abdominal pain, muscle weakness, nausea, diarrhea, muscle inflammation leading to kidney failure, blurred vision, bleeding, dizziness, (etc.).

In addition, some researchers are now questioning the potential cognitive impact statins are having (Alzheimer's, dementia, and confusion), long and short term, due to direct inhibition of the brain's glial cell synthesis of cholesterol (Pfrieger. Science, 9 Nov., 2001; Muldoon. Am J Med, 108 (7); 2000).

There remains a need for improved treatments for hyperlipidemia and/or weight loss.

DISCLOSURE OF THE INVENTION

In one aspect the invention provides a pharmaceutical composition consisting essentially of
(a) choline, or a salt or hydroxide thereof;
(b) niacin, or a salt, amide or ester thereof;
(c) folic acid, or a salt thereof;
(d) methionine or a salt or ester thereof;
(e) glycine or a salt, ester or methylated form thereof, and
(f) optionally a pharmaceutically acceptable carrier and/or excipients.

Preferably the composition also comprises a pharmaceutically acceptable carrier and/or excipients.

In a preferred embodiment the ingredients (a)-(e) are the only active ingredients present.

Preferably the choline is in the form of choline chloride, choline bitartrate, choline base, choline hydroxide.

Preferably the niacin is in the form of niacin, or a salt or nicotinamide.

Preferably the methionine is in the forth of L-methionine or a salt thereof.

Preferably the glycine is trimethylglycine, trimethylated on the amino nitrogen.

More preferably components (a)-(e) are all selected from the preferences above.

These preferences are also preferred in other aspects of the invention.

In another aspect the invention provides a method for preparing a pharmaceutical composition, comprising mixing the following:
(a) choline, or a salt or hydroxide thereof;
(b) niacin, or a salt, amide or ester thereof;
(c) folic acid, or a salt thereof;
(d) methionine or a salt or ester thereof;
(e) glycine or a salt, ester or methylated form thereof; and
(f) one or more pharmaceutically acceptable excipients;
to form a pharmaceutical composition wherein ingredients (a)-(e) are the only active ingredients present.

In another aspect the invention comprises a pharmaceutical composition consisting essentially of
(a) choline, or a salt or hydroxide thereof;
(b) niacin, or a salt, amide or ester thereof;
(c) folic acid, or a salt thereof;
(d) methionine or a salt or ester thereof;
(e) glycine or a salt, ester or methylated form thereof; and
(f) optionally a pharmaceutically acceptable carrier and/or excipients for use in treating hyperlipidemia.

In a further aspect the invention comprises a pharmaceutical composition consisting essentially of
(a) choline, or a salt or hydroxide thereof;
(b) niacin, or a salt, amide or ester thereof;
(c) folic acid, or a salt thereof;
(d) methionine or a salt or ester thereof;
(e) glycine or a salt, ester or methylated form thereof; and
(f) optionally a pharmaceutically acceptable carrier and/or excipients
for use in lowering LDL cholesterol.

In a further aspect the invention comprises a pharmaceutical composition consisting essentially of
(a) choline, or a salt or hydroxide thereof;
(b) niacin, or a salt, amide or ester thereof;
(c) folic acid, or a salt thereof;
(d) methionine or a salt or ester thereof;
(e) glycine or a salt, ester or methylated form thereof; and
(f) optionally a pharmaceutically acceptable carrier and/or excipients for use in weight reduction in humans.

In a further aspect the invention provides a method of treating hyperlipidemia comprising administering a pharmaceutical composition consisting essentially of
(a) choline, or a salt or hydroxide thereof;
(b) niacin, or a salt, amide or ester thereof;
(c) folic acid, or a salt thereof;
(d) methionine or a salt or ester thereof;
(e) glycine or a salt, ester or methylated form thereof; and
(f) optionally a pharmaceutically acceptable carrier and/or excipients to a patient in need thereof.

In a further aspect the invention provides a method of lowering LDL cholesterol in blood comprising administering a pharmaceutical composition consisting essentially of
(a) choline, or a salt or hydroxide thereof;
(b) niacin, or a salt, amide or ester thereof;
(c) folic acid, or a salt thereof;
(d) methionine or a salt or ester thereof;
(e) glycine or a salt, ester or methylated form thereof; and
(f) optionally a pharmaceutically acceptable carrier and/or excipients
to a patient in need thereof.

In a further aspect the invention provides a method for reducing the weight of a patient, comprising administering a pharmaceutical composition consisting essentially of
(a) choline, or a salt or hydroxide thereof;
(b) niacin, or a salt, amide or ester thereof;
(c) folic acid, or a salt thereof;
(d) methionine or a salt or ester thereof;
(e) glycine or a salt, ester or methylated form thereof; and
(f) optionally a pharmaceutically acceptable carrier and/or excipients to a patient in need thereof.

In further aspects there is provided the use of (a)-(e) or (a)-(f) in the preparation of medicaments for the treatment of following conditions:
(i) hyperlipidemia
(ii) elevated LDL cholesterol and
(iii) excess body weight.

Preferably the components (a)-(e) are mixed together in a reactor, or a mixing bowl or in a liquid preparation to form the pharmaceutical composition of the invention. The mixture may also include pharmaceutical excipients, added before, during or after the ingredients (a)-(e).

The pharmaceutical composition is usually for oral administration. It may take any of a variety of forms including being a liquid, a gel, a tablet, a capsule, or a lozenge. Such liquids, tablets, capsules or lozenges may be prepared according to methods known in the pharmaceutical arts, and described in textbooks such as Remington: The Science and Practice of Pharmacy, 20$^{th}$ edition Gennaro et al. Eds Lippincott Williams and Wilkins (2000).

The tablets, capsules and lozenges typically contain from 1% to 95% (w/w) of the active compounds, preferably 5% to 70% (w/w). Suitable excipients include magnesium carbonate, magnesium stearate, talc, lactose, sucrose, glucose, pectin, dextrin, starch, gelatin, tragacanth, methylcellulose, sodium carboxymethylcellulose and the like.

For a liquid form an aqueous composition is currently preferred. The liquid forms include solutions, suspension and emulsions.

The dose to be administered to recipients preferably provides
(a) 0.1 mg-1500 mg choline or a hydroxide or salt thereof;
(b) 0.1 mg-100 mg niacin, or a salt, amide or ester thereof;
(c) 0.01 mg-0.2 mg folic acid, or a salt thereof;
(d) 0.1 mg-100 mg methionine or a salt or ester thereof; and
(e) 0.1 mg-100 mg glycine or a salt, ester or methylated form thereof.

A more preferred dose is:
(a) 100 mg-1000 mg choline or a hydroxide or salt thereof;
(b) 10 mg-50 mg niacin, or a salt, amide or ester thereof;
(c) 0.08 mg-0.1 mg folic acid, or a salt thereof;
(d) 40 mg-100 mg methionine or a salt or ester thereof; and
(e) 20 mg-50 mg glycine or a salt, ester or methylated form thereof.

The most preferred dose is:
(a) 500 mg-1000 mg choline or a hydroxide or salt thereof;
(b) 10 mg-50 mg niacin, or a salt or amide thereof;
(c) 0.8 mg-0.1 mg folic acid, or a salt thereof;
(d) 40 mg-100 mg methionine or a salt thereof; and
(e) 20 mg-50 mg trimethylglycine or a salt thereof.

In other embodiments, the choline or hydroxide or salt is present in a dose of 800-1500 mg. Preferably in this embodiment components (b)-(e) are present in amounts of the preferred, the more preferred or most preferred doses above.

Preferably the solid dosage forms of the pharmaceutical compositions are formulated to provide one dose or half a dose selected from the preferred doses per dosage form, such as a tablet, capsule or lozenge.

Preferably for a liquid pharmaceutical form the formulation is such that a preferred dose is included in 3-300 ml, preferably 5-50 ml of liquid.

In the specification the term "pharmaceutical composition" is intended to include over the counter pharmaceutical composition and compositions that confer health benefits including vitamin compositions.

The term "excipients" means "ingredient(s) other than the choline, niacin, folic acid, methionine or glycine compound listed in (a)-(e). Such ingredients include diluents, flavoring agents, binders, preservatives, tablet disintegrating agents, and encapsulating materials.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

The term "consists essentially of" means that the recited components are present and that additional ingredients may be present in amounts that do not materially affect functioning of the invention.

The invention also provides a pharmaceutical composition comprising
(a) choline, or a salt or hydroxide thereof;
(b) niacin, or a salt, amide or ester thereof;
(c) folic acid, or a salt thereof;
(d) methionine or a salt or ester thereof; and
(e) glycine or a salt, ester or methylated form thereof as the only active ingredients.

In another embodiment, the invention provides a pharmaceutical composition comprising
(a) choline, or a salt or hydroxide thereof;
(b) niacin, or a salt, amide or ester thereof;
(c) folic acid, or a salt thereof;
(d) methionine or a salt or ester thereof; and
(e) glycine or a salt, ester or methylated form thereof for use in treating hyperlipidema.

In a further embodiment, the invention provides a pharmaceutical composition comprising
(a) choline, or a salt or hydroxide thereof;
(b) niacin, or a salt, amide or ester thereof;
(c) folic acid, or a salt thereof;
(d) methionine or a salt or ester thereof; and
(e) glycine or a salt, ester or methylated form thereof for use in lowering LDL cholesterol.

The invention also provides methods for use of these compositions in methods of treating hyperlipidemia and methods for lowering LDL cholesterol respectively.

The preferences of the other aspects of the invention also apply to these aspects.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

EXAMPLES

The following examples further illustrate the invention.

Example I

Preparation of a Composition of the Invention

The invention is a method for quad methylating a choline molecule by mixing, reacting, compounding any molecule of choline with Vitamin B3, Folic Acid, L-Methionine and Tri-methyl glycine. Choline has show to be a trimethylated molecule if it has Vitamin B3, Folic Acid & L-Methione present. The inventor has proven that by Quad methylating Choline with the addition of Tri-methyl-glycine, the effects are greater.

The Quad Methylation Process will take place in a reactor, mixing bowl or liquid preparation. Choline Chloride, Choline Bitartrate, Choline Base, Choline hydroxide, just to mention a few. Any form of choline can be used to obtain the same results. Reactants to be used are Vitamin B3 (Niacin and all forms of niacin), Folic Acid (and all forms of Folate), L-Methionine (and all forms of Methionine) and Glycine (all forms but especially the tri-methyl-glycine form). Different levels of material can also be used to achieve the inventor's desired results.

Example Formulation

| | |
|---|---|
| Choline Base | 1000 mg |
| Niacin | 20 mg |
| Folic Acid | 100 mcg |
| L-Methionine | 50 mg |
| Tri-Methyl-glycine | 50 mg |
| Water | 30 ml |

Example II

Materials and Methods; Experimental Design

Experimental Animals 96 male Wistar rats were supplied from the National Breeding Centre at the Bulgarian Academy of Sciences (Slivnitsa, Bulgaria) and were housed in a controlled environment: temperature 20-22° C., free access to food (either standard food or a 1% cholesterol enriched formula) and water, 12 h alternating light and dark cycles, at the Animal Care facility of the Faculty of Pharmacy, MU-Sofia.

The animals were randomly distributed in sixteen treatment groups, as follows:
1. Untreated control (sacrificed after 4 weeks) (6 animals);
2. Untreated control (sacrificed after 5 weeks) (6 animals);
3. Untreated control (sacrificed after 6 weeks) (6 animals);
4. Untreated control (sacrificed on the $31^{st}$ day) (6 animals);
5. Positive control (HCD) (sacrificed after 4 weeks) (6 animals);
6. Positive control (HCD) (sacrificed after 5 weeks) (6 animals);
7. Positive control (HCD) (sacrificed after 6 weeks) (6 animals);
8. HC D animals, treated with the test composition of Example I (TCE1) (1 ml/kg/day) (sacrificed after 4 weeks) (6 animals);
9. HC D animals, treated with TCE1 (1 ml/kg/day) (sacrificed after 5 weeks) (6 animals);
10. HC D animals, treated with TCE1 (1 ml/kg/day) (sacrificed after 6 weeks) (6 animals);
11. HC D animals, treated with TCE1 (0.5 ml/kg/day) (after 4 weeks) (6 animals);
12. HC D animals, treated with TCE1 (0.5 ml/kg/day) (sacrificed after 5 weeks) (6 animals);
13. HC D animals, treated with TCE1 (0.5 ml/kg/day) ((sacrificed after 6 weeks) (6 animals);
14. HC D animals, treated with TCE1 (0.25 ml/kg/day) (sacrificed after 4 weeks) (6 animals);
15. HC D animals, treated with TCE1 (0.25 ml/kg/day) (sacrificed after 5 weeks) (6 animals);
16. HC D animals, treated with TCE1 (0.25 ml/kg/day) (sacrificed after 6 weeks) (6 animals);

Treatment

The experiments were carried out in accordance with the requirements of the European Convention for Protection of Vertebrate Animals used for Experimental and other Specific Purposes (1991). Healthy, pathogen free male Wistar rats were used in this study, whereby every experimental group consisted of 10 animals. The exposure to the 1% cholesterol-enriched diet (HCD) was commenced 2 weeks prior to the treatment with either the test composition or purified water (in the control groups). The treatment was carried out using a gastric tube and the daily dose was divided in two administration carried out at 10.00 a.m. and 04.00 p.m. The animals were treated for 4, 5 or 6 weeks and sacrificed accordingly.

Serum Lipid Measurements

Animals were sacrificed, blood samples were collected via cardial function and thereafter the serum fractions were isolated. The determination of serum lipids levels was carried out using standard methods. These tests included total cholesterol (TC), low-density lipoprotein cholesterol, (LDL-C), high-density lipoprotein cholesterol, (HDL-C), triglycerides (TG). The TC/HDL ratio as well as the atherogenic indices ((TC-HDL-C)/HDL-C) were determined as well.

Post-Mortal Evaluation

After collecting the blood samples the carcasses were necropsied by a qualified vet surgeon, and the visceral organs (liver, spleen, stomach, intestines) were examined for gross signs of toxicity. Moreover the animal body mass was monitored on regular basis as a non-specific marker of general toxicity.

Data Processing and Statistics

The results from lipid level investigations were statistically evaluated using a paired Student's t-test and post hoc Dunnet test, using BMD P4V, BMD P3D and BMD P7D software.

Experimental Results

As evident from the presented data (Tables 1-3), exposure to the HCD food was consistent with a significant increase in total cholesterol and LDL-C as compared to the rats fed standard diet.

Treatment with the composition of Example I was consistent with a strong, statistically significant protection of animals against the hyperlipidemic effects of the cholesterol enriched diet. The effect generally was dose-dependent and especially prominent after 5 and 6 weeks treatment.

A characteristic feature of the biological activity of new composition was the striking lowering of the LDL cholesterol especially following longer treatment periods of 5 weeks or more. These favorable hyperlipidemic effects were more pronounced at the higher dose levels of 1 ml/kg/day or 0.5 ml/kg/day.

Throughout the study period there was neither mortality nor alteration in the feeding behavior of treated animals as compared to the untreated controls. The post mortem examination of the visceral organs failed to reveal any signs of toxic deleterious effects in the treatment groups, as compared to the controls. Moreover the exposure of animals to the new composition caused no alterations in the weight gain rates of treated vs untreated animals.

Taken together these findings indicate that the new composition exerts prominent modulating effects on serum lipids in a model of high-cholesterol diet induced dislipidemia in the rat. At the same time the formula is virtually devoid of gastric mucosa irritating or general toxic effects within the tested dose intensity range and within the studied exposure period.

TABLE 1

Hypolipidemic effects of the test composition of Example I (TCE1) in high-cholesterol diet (HCD)-induced hyperlipidemic rats after 4 weeks treatment. The data represent mean values ± SD (n = 6) of the plasma levels of total cholesterol, LDL-cholesterol, HDL-cholesterol, triglycerides (mmol/L).

| Parameters | Control | | HCD | | HCD + 1 ml/kg | | HCD + 0.5 ml/kg | | HCD + 0.25 ml/kg | |
|---|---|---|---|---|---|---|---|---|---|---|
| | mean | sd | mean | sd | mean | sd | mean | sd | mean | sd |
| LDL | 0.20 | 0.09 | 0.69 | 0.12 | 0.08* | 0.06 | 0.08 | 0.03 | 0.10* | 0.06 |
| Total cholesterol | 1.89 | 0.10 | 2.31 | 0.25 | 1.53* | 0.13 | 1.76* | 0.1 | 1.93* | 0.28 |
| HDL-Cholesterol | 1.38 | 0.11 | 1.08 | 0.18 | 0.90* | 0.11 | 0.98 | 0.16 | 1.01* | 0.24 |
| Triglycerides | 0.67 | 0.22 | 2.10 | 0.27 | 1.22* | 0.02 | 1.54* | 0.44 | 1.82* | 0.51 |

TABLE 1-continued

Hypolipidemic effects of the test composition of Example I (TCE1) in high-cholesterol diet (HCD)-induced hyperlipidemic rats after 4 weeks treatment. The data represent mean values ± SD (n = 6) of the plasma levels of total cholesterol, LDL-cholesterol, HDL-cholesterol, triglycerides (mmol/L).

| Parameters | Control mean | sd | HCD mean | sd | HCD + 1 ml/kg mean | sd | HCD + 0.5 ml/kg mean | sd | HCD + 0.25 ml/kg mean | sd |
|---|---|---|---|---|---|---|---|---|---|---|
| Atherogenic index | 0.38 | 0.13 | 1.18 | 0.30 | 0.72* | 0.10 | 0.84* | 0.36 | 0.97* | 0.35 |
| TC/LDL | 1.38 | 0.13 | 2.18 | 0.30 | 1.72* | 0.10 | 1.84* | 0.36 | 1.97* | 0.35 |

*p < 0.05 vs. the positive HCD control (Student's t-test);
**p < 0.01 vs. the positive HCD control (Student's t-test);

TABLE 2

Hypolipidemic effects of TCE1 in high-cholesterol diet (HCD)-induced hyperlipidemic rats after 5 weeks treatment. The data represent mean values ± SD (n = 6) of the plasma levels of total cholesterol, LDL-cholesterol, HDL-cholesterol, triglycerides (mmol/L).

| Parameters | Control mean | sd | HCD mean | sd | HCD + 1 ml/kg mean | sd | HCD + 0.5 ml/kg mean | sd | HCD + 0.25 ml/kg mean | sd |
|---|---|---|---|---|---|---|---|---|---|---|
| LDL | 0.15 | 0.23 | 1.26 | 0.49 | 0.03** | 0.01 | 0.03** | 0.03 | 0.04** | 0.02 |
| Total cholesterol | 1.30 | 0.29 | 3.47 | 0.30 | 1.54* | 0.19 | 1.31* | 0.06 | 1.51* | 0.13 |
| HDL-Cholesterol | 0.66 | 0.13 | 1.02 | 0.15 | 0.88* | 0.19 | 0.50* | 0.10 | 0.82* | 0.09 |
| Triglycerides | 1.09 | 0.23 | 2.04 | 0.50 | 1.15* | 0.12 | 1.71* | 0.24 | 1.44* | 0.40 |
| Atherogenic index | 1.01 | 0.55 | 2.44 | 0.32 | 0.81** | 0.41 | 1.68* | 0.54 | 0.87* | 0.30 |
| TC/LDL | 2.01 | 0.55 | 3.44 | 0.32 | 1.81* | 0.41 | 2.68* | 0.54 | 1.87* | 0.30 |

*p < 0.05 vs. the positive HCD control (Student's t-test),
**p < 0.01 vs. the positive HCD control (Student's t-test);

TABLE 3

Hypolipidemic effects of TCE1 in high-cholesterol diet (HCD)-induced hyperlipidemic rats after 6 weeks treatment. The data represent mean values ± SD (n = 6) of the plasma levels of total cholesterol, LDL-cholesterol, HDL-cholesterol, triglycerides (mmol/L).

| Parameters | Control mean | sd | HCD mean | sd | HCD + 1 ml/kg mean | sd | HCD + 0.5 ml/kg mean | sd | HCD + 0.25 ml/kg mean | sd |
|---|---|---|---|---|---|---|---|---|---|---|
| LDL | 0.30 | 0.08 | 2.10 | 0.14 | 0.26* | 0.23 | 0.19** | 0.07 | 0.26* | 0.13 |
| Total cholesterol | 1.11 | 0.23 | 4.08 | 0.30 | 1.54* | 0.26 | 1.83* | 0.20 | 1.73* | 0.20 |
| HDL-Cholesterol | 0.69 | 0.15 | 1.02 | 0.18 | 1.22* | 0.22 | 1.32* | 0.31 | 0.93* | 0.41 |
| Triglycerides | 0.81 | 0.26 | 3.08 | 0.68 | 1.48* | 0.28 | 1.53* | 0.49 | 1.44* | 0.18 |
| Atherogenic index | 0.62 | 0.17 | 3.12 | 0.97 | 0.27** | 0.12 | 0.41* | 0.14 | 1.09* | 0.67 |
| TC/LDL | 1.62 | 0.17 | 4.12 | 0.97 | 1.27* | 0.12 | 1.41* | 0.14 | 2.09* | 0.67 |

*p < 0.05 vs. the positive HCD control (Student's t-test);
**p < 0.01 vs. the positive HCD control (Student's t-test);

Example III

Human Study Showing Lowering of Body Fat % and Body Weight

Procedure

Three healthy humans were used for this pre-clinical study. Two females and one male. No changes were made to any of the subject's diets, exercise programs or life styles. The composition of Example I was administered as follows in a liquid form:

Week 1 5 ml 20 minutes before breakfast

Week 2 5 ml twice per day. Once 20 minutes before breakfast and once 20 minutes before lunch Week 3 through Week 6 5 ml three times per day. Once 20 minutes before breakfast, once 20 minutes before lunch and once 20 minutes before dinner.

Results

First Six Weeks

Female Subject 1:

Starting Body Fat %: 43.3%

Starting Body Weight: 218.5 lbs

Ending Body Fat % 31.0%

Ending Body Weight: 205.2

Total body % weight loss of 12.3% and 13.3 lbs.

Second Six Weeks

Subject one continued testing for an additional 6 weeks with the following results:

Body Fat % dropped to 19% for an additional loss of 12%

Body Weight dropped to 178.5 or an additional 26.7

First Six Weeks

Female Subject 2:

Starting Body Fat %: 30.0%

Starting Body Weight: 184 lbs

Ending Body Fat % 26.8

Ending Body Weight: 166.8 lbs

Total body % weight loss of 3.2% and 17.2 lbs

First Six weeks:

Male Subject 1:

Starting Body Fat %: 19.0%

Starting Body Weight: 242 lbs

Ending Body Fat %: 10.0%

Ending Body Weight: 232 lbs

Total body % weight loss of 9% and 10 lbs.

Conclusion:

In this pre-clinical study, the composition of the invention significantly lowered body fat percent and total body weight. Each subject reported having more energy, feeling leaner and just felt much better all around. No side effects were reported:

Product recognized as safe and effective.

The above samples are illustrations of the practice of the invention. It will be appreciated by those skilled in the art that the invention can be carried out with numerous modifications and variations. For example different doses of the active ingredients may be used, and the carriers and excipients used may be varied.

Example IV

Rat Study 2: Weight Loss without Toxicity

Procedure

Six Sprague-Dawley white albino rats (all male), eight weeks of age, weighing between 201-291 grams each, were used for the study. Animals remained in a separate cage for the duration of the study. After a seven day acclimation period, each animal was visually examined, weighed and assigned a number. Each tail was marked with a color code for easy identification. Animals received either the diluents of the Test Formulation the Test Formula at 1× concentration (the amount representing a single adult human dose), or 10× concentration of the Test Formula (representing 10× the normal human dose) daily, via syringe feeding, for a total of 30 days. All animals were maintained on standard rat chow and had free access to both food and water at all times. But, after the first week junk food was added to the diet. (candy bars, cookies, etc) Animals were inspected daily for skin lesions and behavioral abnormalities, and weighed at regular intervals. At the conclusion of the test, all animals were sacrificed via an overdose injection of Beuthanafia—D (I.P.). Tissue from heart, liver, kidney, and upper G.I. tract were removed from each animal, fixed according to the recommended protocol, and submitted for histopathologic examination.

Results

No definitive histopathologic substance-related tissue toxicity was confirmed in any of the samples. It was noted that animal started losing weight from week 2-4 even though they were on a high calorie junk food diet. Product recognized as safe and will move on to phase II toxicity study.

Example V

Rat Study 3: Weight Loss without Toxicity

Procedure

Eighteen Sprague-Dawley white albino rats (nine males and nine females), eight weeks of age, weighing between 201-291 grams each, were divided equally by gender into three groups of six animals each. Animals remained in a separate cage for the duration of the study. After a five day acclimation period, each animal was visually examined, weighed and assigned a number. Each tail was marked with a color code for easy identification. Animals received either the diluents of the Test Formulation of Example I—[orange juice], the Test Formula at 1× concentration (the amount representing a single adult human dose), or 10× concentration of the Test Formula (representing 10× the normal human dose) daily, via syringe feeding, for a total of 30 days. All animals were maintained on standard rat chow and had free access to both food and water at all times. Animals were inspected daily for skin lesions and behavioral abnormalities, and weighed at regular intervals. At the conclusion of the test, all animals were sacrificed via an overdose injection of Beuthanafia—D (I.P.). Tissue from heart, liver, kidney, and upper G.I. tract were removed from each animal, fixed according to the recommended protocol, and submitted for histopathologic examination.

Results

No definitive histopathologic substance-related tissue toxicity was confirmed in any of the samples. It was noted that all animals from both the 1× and 10× treatment groups lost interest in their food towards the end of the study indicating a loss of appetite. Product recognized as safe.

The invention claimed is:

1. A pharmaceutical composition consisting essentially of
   (a) choline, or a salt or hydroxide thereof;
   (b) niacin, or a salt, amide or ester thereof;
   (c) folic acid, or a salt thereof;
   (d) methionine or a salt or ester thereof;
   (e) glycine or a salt, ester or methylated form thereof, and
   (f) optionally a pharmaceutically acceptable carrier and/or excipients.

2. The pharmaceutical composition of claim 1 in which ingredients (a)-(e) are active ingredients and are the only active ingredients present.

3. The pharmaceutical composition of claim 1 wherein the choline is in a form selected from the group consisting of choline chloride, choline bitartrate, choline base and choline hydroxide.

4. The pharmaceutical composition of claim 1 wherein the niacin is present as niacin or a salt thereof, or as nicotinamide.

5. The pharmaceutical composition of claim 1 wherein the methionine is present as L-methionine or a salt thereof.

6. The pharmaceutical composition of claim 1 wherein the methylated form of glycine is trimethylglycine, trimethylated on amino nitrogen.

7. The pharmaceutical composition of claim 2 in which
(a) the choline salt or hydroxide thereof is choline chloride, choline bitartrate, choline base or choline hydroxide;
(b) the niacin or salt, amide or ester thereof is present as niacin or a salt thereof or nicotinamide;
(c) the folic acid is present as folic acid or a salt thereof;
(d) the methionine or a salt or ester thereof is present as L-methionine or a salt thereof; and
(e) the glycine or a salt, ester or methylated form thereof is present as trimethylglycine.

8. A method of treating hyperlipidemia consisting essentially of administering a pharmaceutical composition that consists essentially of
(a) choline, or a salt or hydroxide thereof;
(b) niacin, or a salt, amide or ester thereof;
(c) folic acid, or a salt thereof;
(d) methionine or a salt or ester thereof;
(e) glycine or a salt, ester or methylated form thereof, and
(f) optionally a pharmaceutically acceptable carrier and/or excipients to a patient in need thereof.

9. A method of lowering LDL cholesterol in blood comprising administering a pharmaceutical composition consisting essentially of
(a) choline, or a salt or hydroxide thereof;
(b) niacin, or a salt, amide or ester thereof;
(c) folic acid, or a salt thereof;
(d) methionine or a salt or ester thereof;
(e) glycine or a salt, ester or methylated form thereof, and
(f) optionally a pharmaceutically acceptable carrier and/or excipients to a patient in need thereof.

10. A method for reducing the weight of a patient, comprising administering a pharmaceutical composition consisting essentially of
(a) choline, or a salt or hydroxide thereof;
(b) niacin, or a salt, amide or ester thereof;
(c) folic acid, or a salt thereof;
(d) methionine or a salt or ester thereof;
(e) glycine or a salt, ester or methylated form thereof, and
(f) optionally a pharmaceutically acceptable carrier and/or excipients to a patient in need thereof.

11. The pharmaceutical composition of claim 1 which is a tablet, capsule or lozenge comprising from 1% to 95% (w/w) of the active compounds.

12. The pharmaceutical composition of claim 1 which is an aqueous composition.

13. The composition of claim 1 formulated to provide a dose of
(a) 0.1mg -1500 mg choline or a hydroxide or salt thereof;
(b) 0.1 mg -100 mg niacin, or a salt, amide or ester thereof;
(c) 0.01 mg -0.2 mg folic acid, or a salt thereof;
(d) 0.1 mg -100 mg methionine or a salt or ester thereof; and
(e) 0.1 mg -100 mg glycine or a salt, ester or methylated form thereof.

14. The composition of claim 13 formulated to provide a dose of
(a) 100 mg -1000 mg choline or a hydroxide or salt thereof;
(b) 10 mg -50 mg niacin, or a salt, amide or ester thereof;
(c) 0.08mg -0.1 mg folic acid, or a salt thereof;
(d) 40 mg -100 mg methionine or a salt or ester thereof; and
(e) 20 mg -50 mg glycine or a salt, ester or methylated form thereof.

15. The composition of claim 14 formulated to provide a dose of
(a) 500 mg -1000 mg choline or a hydroxide or salt thereof;
(b) 10mg -50 mg niacin, or a salt or amide thereof;
(c) 0.8mg -0.1 mg folic acid, or a salt thereof;
(d) 40 mg -100 mg methionine or a salt thereof; and
(e) 20 mg -50 mg trimethylglycine or a salt thereof.

16. The composition of claim 13 which is formulated as a liquid pharmaceutical form so that the dose is present either in (i) 3-300 ml of liquid, or (ii) in 5-50 ml of liquid.

17. The method of claim 8 wherein 800-1500 mg of choline or a salt or a hydroxide thereof are administered.

18. The method of claim 9 wherein 800-1500 mg of choline or a salt or a hydroxide thereof are administered.

19. A method of treating hyperlipidemia comprising administering a pharmaceutical composition comprising
(a) choline, or a salt or hydroxide thereof;
(b) niacin, or a salt, amide or ester thereof;
(c) folic acid, or a salt thereof;
(d) methionine or a salt or ester thereof; and
(e) glycine or a salt, ester or methylated form thereof to a patient in need thereof.

20. A method of lowering LDL cholesterol in blood comprising administering a pharmaceutical composition comprising
(a) choline, or a salt or hydroxide thereof;
(b) niacin, or a salt, amide or ester thereof;
(c) folic acid, or a salt thereof;
(d) methionine or a salt or ester thereof; and
(e) glycine or a salt, ester or methylated form thereof; to a patient in need thereof.

21. The method of claim 10 wherein 800-1500 mg of choline or a salt or hydroxide thereof are administered.

* * * * *